United States Patent [19]
Hall et al.

[11] Patent Number: 5,493,911
[45] Date of Patent: Feb. 27, 1996

[54] SYSTEM FOR MEASURING THE ULTRASONIC VELOCITY IN THE THICKNESS DIRECTION OF MOVING WEBS WITHOUT ERRORS DUE TO DELAYS IN THE ONSET OF DIGITIZATION

[75] Inventors: Maclin S. Hall, Marietta; Pierre H. Brodeur, Smyrna; Theodore G. Jackson, Atlanta, all of Ga.

[73] Assignee: Institute of Paper Science and Technology, Inc., Atlanta, Ga.

[21] Appl. No.: 380,379

[22] Filed: Jan. 30, 1995

Related U.S. Application Data

[63] Continuation of Ser. No. 971,048, Nov. 30, 1992, abandoned.

[51] Int. Cl.$^6$ .................................................. G01N 29/18
[52] U.S. Cl. ............................... 73/597; 73/598; 73/639; 73/159
[58] Field of Search ........................... 73/597, 598, 159, 73/602, 627, 628, 629, 639, 644, 635

[56] References Cited

U.S. PATENT DOCUMENTS

| | | | |
|---|---|---|---|
| 4,174,636 | 11/1979 | Pagano . | |
| 4,291,577 | 9/1981 | Baum et al. | 73/597 |
| 4,574,634 | 3/1986 | Pappano . | |
| 4,688,423 | 8/1987 | Orkosalo | 73/598 |

(List continued on next page.)

OTHER PUBLICATIONS

"Using a Robot–Based Instrument to Measure the In–Plane Ultrasonic Velocities of Paper" by C. C. Habeger, M. L. Van Zummeren and W. A. Wink, *Tappi Journal*, pp. 171–175, Jul. 1989.
"On–Machine Sensors To Measure Paper Mechanical Properties" by Maclin S. Hall, Sensors Expo West Proceedings 1990, pp. 205A–1–205A–4.
"On–Line Ultrasonic Measurement of Paper Strenth" by Maclin S. Hall, *Sensors*, Jun. 1990, pp. 13–20.
"Acousto–Ultrasonic Measurement Of Internal Bond Strength In Composite Wood Products" by John M. Rodgers, Allen T. Green and Stephen W. Borup, *Materials Evaluation*, May 1991, pp. 566–571.
"Ultrasonic Testing of Materials" by Joseph Krautkramer and Herbert Krautkramer, Third Edition, 1983, p. 302.
"On–Machine Sensors To Measure Paper Mechanical Properties" by M. Hall, P. Brodeur, K. Lorenz and T. Jackson, Presented at DOE/Industry Sensors Technical Conference in Nov. 1990.
"Sound Wave Dispersion And Attenuation In The Thickness Direction Of Paper" by P. Brodeur and M. S. Hall, Proceedings 1991 International Paper Physics Conference, Sep. 1991, pp. 109–114.
"Thickness Direction Measurements in Paper Materials using Ultrason Sensors immersed in water–filled wheels" by Brodeur et al., Jul. 1991, pp. 331–334.
"On Machine Sensors to measure Paper Mechanical Properties", Hall et al., Nov. 11, 1991.
"On Machine Sensors to Measure Paper Mechanical Properties", Hall et al., Oct. 1988.

*Primary Examiner*—Hezron E. Williams
*Assistant Examiner*—Nashmiya Ashraf
*Attorney, Agent, or Firm*—Fitch, Even, Tabin & Flannery

[57] ABSTRACT

A system for relatively accurately measuring the velocity and time of flight of ultrasonic signals in the thickness direction through moving web-like materials, such as paper, paperboard and the like, includes a pair of ultrasonic transducers disposed on opposing sides of the moving web-like material. The ultrasonic transducers are disposed in fluid-filled wheels to provide acoustical coupling between the transducers and the web-like material. In order to eliminate errors, known as trigger jitter, inherent in systems used to digitize ultrasonic signals for manipulation by a digital computer, a pulse echo box is provided to enable the capture of a reflected ultrasonic signal in addition to the ultrasonic signal transmitted through the web. By cross-correlating the transmitted and reflected ultrasonic signals in the same sample period, the error associated with trigger jitter is eliminated.

8 Claims, 8 Drawing Sheets

U.S. PATENT DOCUMENTS

| | | |
|---|---|---|
| 4,713,572 | 12/1987 | Bokowski et al. . |
| 4,730,492 | 3/1988 | Burk . |
| 4,735,087 | 4/1988 | Hourani et al. ............... 73/639 |
| 4,750,368 | 6/1988 | Shearer et al. . |
| 4,769,571 | 9/1988 | Habeger, Jr. et al. . |
| 4,841,223 | 6/1989 | Baum et al. . |
| 5,048,340 | 9/1991 | Thompson et al. ............. 73/597 |
| 5,117,698 | 6/1992 | Baumoel . |
| 5,398,538 | 3/1995 | Williams et al. ............... 73/597 |

SYSTEM FOR MEASURING THE ULTRASONIC VELOCITY IN THE THICKNESS DIRECTION OF MOVING WEBS WITHOUT ERRORS DUE TO DELAYS IN THE ONSET OF DIGITIZATION

This is a continuation, of application Ser. No. 07/971,048, filed Nov. 3, 1992 now abandoned.

BACKGROUND OF THE INVENTION

1. Field of the Invention

The present invention relates to a method for improving the accuracy of non-destructive and non-intrusive testing techniques of moving web-like materials, such as paper, paperboard and other porous materials produced by the paper industry and, in particular, a system for correcting certain inaccuracies generally inherent with ultrasonic testing systems.

2. Description of the Prior Art

Web-like materials, such as paper, paperboard and the like are required to meet particular mechanical property specifications. Normal quality control techniques require that the web-like materials be tested to ensure that the web uniformly meets the desired mechanical property specification.

Destructive-type tests are known for measuring mechanical properties of such web-like materials. Such destructive tests are normally conducted off line on representative samples of the web. There are various problems with such off-line destructive testing. For example, such testing is relatively time consuming and requires production to be stopped or sampled periodically when product is received from the machine. In addition, since such testing is destructive, it is normally performed on representative samples of the web which may be taken, for example, every several thousand of square feet of material. In such a situation, a substantial amount of waste is incurred if the web-like material is found to fail the test.

In order to solve the problems associated with such destructive test type measurements of mechanical properties of web-like materials, ultrasonic testing techniques have been developed. Such testing is done on-line and thus is relatively quicker than off-line destructive testing, while at the sane time provides relatively continuous indication of various mechanical properties of the web-like material to assure virtually uniform quality of the product while minimizing waste.

In known ultrasonic systems for testing various mechanical properties, two ultrasonic transducers are provided. The ultrasonic transducers are generally disposed on opposing sides of the web to allow ultrasonic signals to be transmitted in a direction generally normal to the plane of the web. In such a system, one transducer acts as a transmitter while the other transducer as a receiver. The time of flight of an ultrasonic signal through the thickness of the web is sensed to determine various mechanical properties of the web. In particular, the time of flight of the ultrasonic signal through the thickness of the web is determined by measuring the time of flight of the ultrasonic signal between the transducers during a condition when there is no web or sample present and then measuring the time of flight of the ultrasonic signal during a condition when a web is disposed between the transducers. Generally speaking, the difference in the times of flight during the two conditions is representative of the time of flight of the ultrasonic signal through the web.

There are several known problems with such known ultrasonic testing systems. More specifically, such ultrasonic testing systems normally utilize a digitizing oscilloscope for converting the ultrasonic signals to digital values in order to enable the time of flight to be computed by a digital computer. Such digitizing oscilloscopes are subject to errors from a phenomenon known as "trigger jitter". Trigger jitter in general relates to the unpredictability in the difference in time between the receipt of a trigger signal at the digitizing oscilloscope and the onset of the analog-to-digital conversion. Since this time period can vary with each sample period, cross-correlation of time of flight data with and without a sample present can result in certain inaccuracies in the time of flight measurements and, in turn, the mechanical property being tested.

Another source of error in the time of flight measurement in such ultrasonic testing systems relates to variances in the acoustic path between the two transducers. More particularly, such ultrasonic transducers, normally formed from ceramic or plastic piezoelectric material, are disposed in fluid-filled wheels in order to provide acoustical coupling of the ultrasonic signals relative to the web-like material. Such transducers are fixed in place and attached to axes about which the wheels rotate. Variances in the thickness of the wheels about their circumference can cause errors in the flight time measurements resulting in inaccurate mechanical property measurements.

SUMMARY OF THE INVENTION

It is an object of the present invention to solve the problems associated with the prior art.

It is another object of the present invention to improve the accuracy of on-line tests of web-like materials such as paper, paperboard and other porous materials produced by the paper industry.

It is yet another object of the present invention to provide a system for making continuous tests of moving web-like materials.

It is yet another object of the present invention to compensate for errors in time of flight measurements of ultrasonic signals due to trigger jitter.

It is yet another object of the present invention to provide a method for making non-destructive tests on a moving web of material which incorporates ultrasonic transducers disposed in fluid-filled wheels which compensates for variations in the transducer wheel thickness of the fluid-filled wheels about their circumference.

Briefly, the present invention relates to a method for improving the accuracy of measuring the time of flight and velocity of ultrasonic signals through moving web-like materials, such as paper, paperboard and the like, which includes a pair of ultrasonic transducers disposed on opposing sides of the moving web-like material. In order to provide acoustical coupling between the transducers and the web-like material, the transducers are disposed within fluid-filled wheels. Errors due to variances in the wheel thicknesses about their circumference which can affect time of flight measurements and ultimately the mechanical property being tested are compensated by averaging the ultrasonic signals for a predetermined number of revolutions of the wheels. The invention further includes a method for compensating for errors resulting from the digitization of the ultrasonic signals. More particularly, the invention includes a method for eliminating errors, known as trigger jitter, inherent with digitizing oscilloscopes used to digitize the signals for manipulation by a digital computer. In particular, rather than cross-correlate ultrasonic signals taken during different sample periods as is known in the art in order to determine the time of flight of the ultrasonic signal through the moving web, a pulse/echo box is included which enables cross-correlation of predetermined transmitted ultrasonic signals with predetermined reflected ultrasonic or echo signals during the sample period. By cross-correlating ultrasonic signals in the same sample period, the error associated with trigger jitter is eliminated.

BRIEF DESCRIPTION OF THE DRAWING

These and other objects of the present invention will be readily understood with reference to the following specification and attached drawing, wherein.

DETAILED DESCRIPTION OF THE INVENTION

Figure 1:
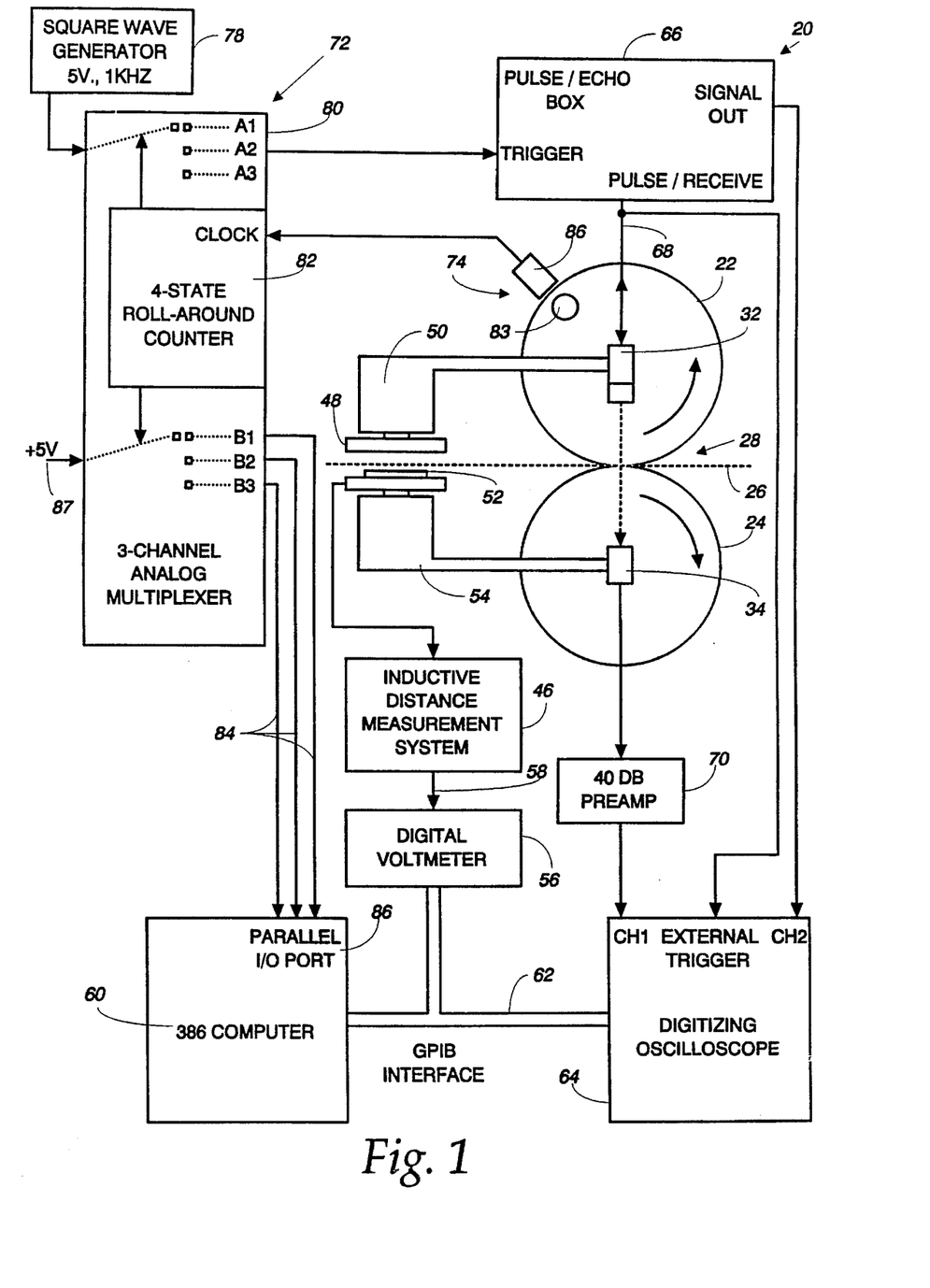
FIG. 1 is a block diagram of an exemplary ultrasonic system for implementing the method in accordance with the present invention.

A system in accordance with the present invention for improving the accuracy of an on-line ultrasonic testing system is illustrated in FIG. I and generally identified with the reference numeral 20. The system 20 includes a pair of fluid-filled wheels and, in particular, a top wheel 22 and bottom wheel 24. The fluid-filled wheels 22 and 24 are disposed about mutually parallel axes (not shown); the distance between which is adjusted so that the fluid-filled wheels 22 and 24 are in contact with each other when there is no sample present. During operation, web-like materials or samples 26, such as paper, paperboard and other such porous products generally produced by the paper industry, are fed into a nip 28 at the interface between the fluid-filled wheels 22 and 24 as generally shown in FIG. 1.

Generally speaking, the times of flight of certain ultrasonic signals between the fluid-filled wheels 22 and 24 both with and without a sample present are used to determine the time of flight and velocity of an ultrasonic signal through a web-like material. The time of flight of the ultrasonic signal is, in turn, used to determine various mechanical properties of the web-like material 26 in a non-destructive and non-intrusive manner while the web-like material 26 is moving along a production line. By providing a continuous and non-destructive method for determining the time of flight and, in turn, various mechanical properties of web-like material 26, quality control of the web 26 is thus greatly improved while at the same time the cost of producing a high quality web is significantly decreased.

However, various errors in known ultrasonic testing systems have been found to affect the accuracy of the time of flight measurements. These errors, in turn, affect the accuracy of the mechanical properties that are based on the time of flight measurements. These error sources relate to variances in the transducer wheel thickness about their circumference and unpredictable and varying time delays at the onset of the analog-to-digital conversion process known as "trigger jitter".

Trigger Jitter

The errors in time of flight measurements associated with trigger jitter are inherent in known digitizing oscilloscopes used to convert the ultrasonic signals to digital signals to enable the signals to be manipulated by a digital computer. In particular, it is known to cross-correlate certain digitized ultrasonic signals during a sampling period when no sample 26 is present in the nip 28 with certain stored digitized ultrasonic signals during a different sampling period when a sample 26 is present in the nip 28 to determine the time of flight of an ultrasonic signal through the web 26.

Figure 2:
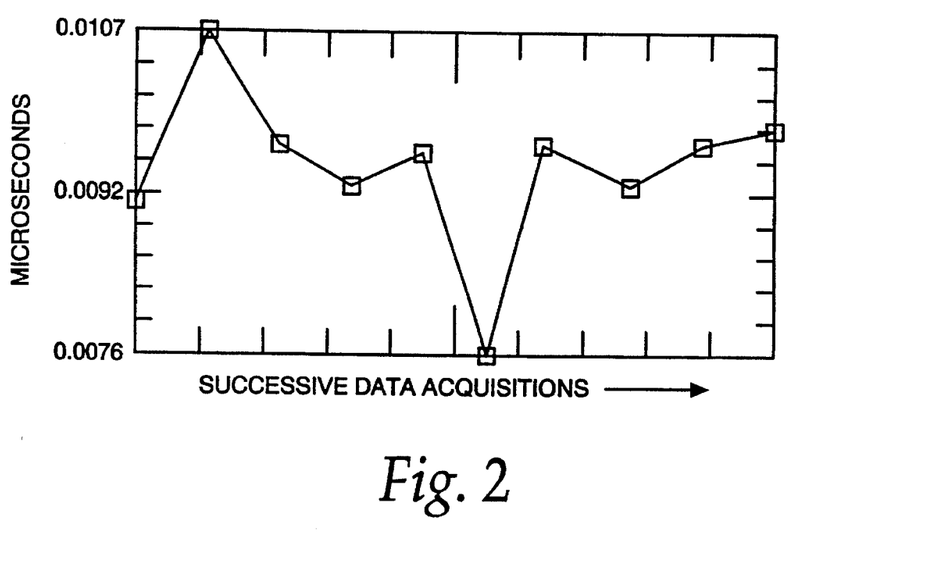
FIG. 2 is an exemplary curve illustrating the errors associated with trigger jitter of a current ultrasonic signal cross-correlated with a stored representation of the same signal as a function of successive data acquisitions.

However, cross-correlation of ultrasonic signals during different sampling periods can result in certain errors. Such errors, known as trigger jitter, relate to the unpredictable delay from the time the digitizing oscilloscope is triggered and the onset of the analog-to-digital conversion process. Such delays can be significant as shown in FIG. 2 which illustrates the effects of trigger jitter when a current waveform is cross-correlated with a previously-stored representation of the same waveform. In particular, FIG. 2 illustrates the error in microseconds on the vertical axis when an exemplary current waveform is cross-correlated with a stored representation of the same waveform as a function of successive data acquisitions.

Figure 3:
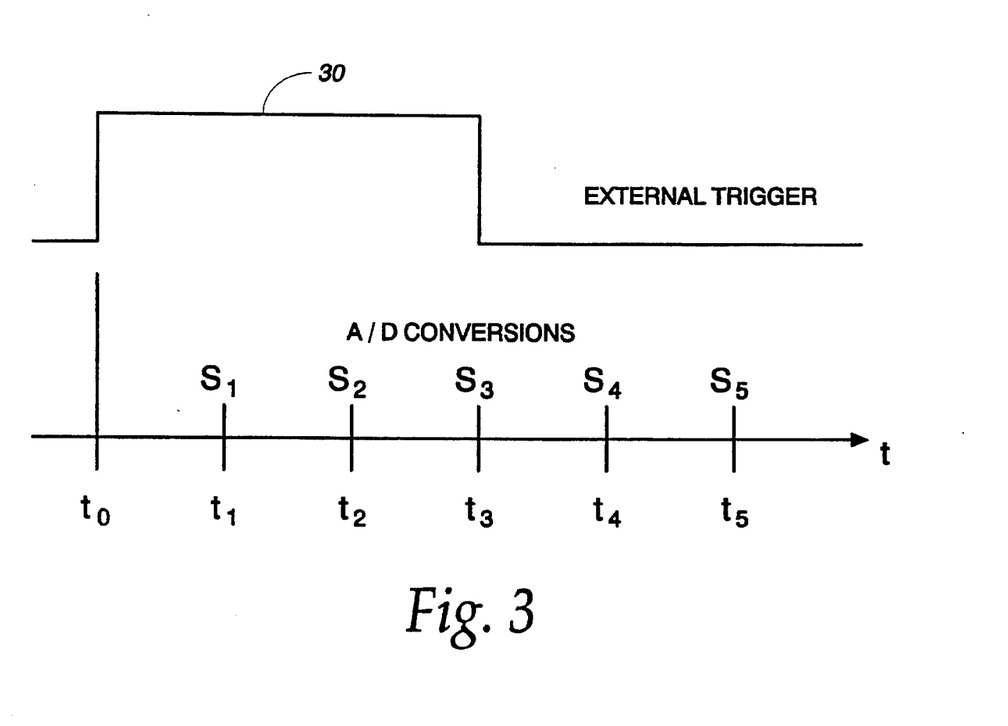
FIG. 3 is an exemplary curve illustrating an external trigger signal as a function of the analog-to-digital conversion times for a known digitizing oscilloscope.

The nature of trigger jitter problem is best understood with reference to FIG. 3. More particularly, FIG. 3 illustrates an exemplary trigger signal 30 as a function of time. The time scale along the horizontal axis represents exemplary analog-to-digital conversion times $t_1 \ldots t_5$. As shown, the trigger signal 30 is received at time $t_0$ while a plurality of sample points $S_1 \ldots S_5$ are shown as being converted at times $t_1 \ldots t_5$, respectively.

In certain digitizing oscilloscopes used for such ultrasonic testing, it has been determined that the time period $(t_1-t_0)$ is unpredictable and can vary per sampling period. The time $t_1$ represents the time at which the digital conversion begins, e.g., digital conversion of the first sample point $s_1$. It has also been determined that the time period $t_1-t_0$ is not necessarily equal to the time period between subsequent conversions. In other words although $(t_3-t_4)=(t_4-t_3)=(t_3-t_2)=(t_2-t_1)=\Delta t$, $t_1-t_0$ is generally not equal to $\Delta t$. This leads to uncertainty and unpredictability of the time period $t_1-t_0$, known as "trigger jitter". Due to the accuracy required in ultrasonic measurements, such trigger jitter can lead to significant errors as illustrated in FIG. 2 when the digitized ultrasonic signals are cross-correlated from different sampling periods. More particularly, in known digitized ultrasonic systems, current ultrasonic signals have known to be cross-correlated with stored or reference digitized ultrasonic signals. Since such current and stored signals are digitized in response to different trigger signals 30 (e.g., during different sample periods), a certain degree of error due to trigger jitter will occur when the two ultrasonic signals are cross-correlated. The system in accordance with the invention solves this problem by virtually eliminating the error due to trigger jitter. In particular, as will be discussed in detail below, the system avoids cross-correlation of ultrasonic signals during different sampling periods. More specifically, the system in accordance with the present invention cross-correlates ultrasonic signals during the same sampling period and thus essentially eliminates any errors due to trigger jitter.

Variance in Transducer Wheel Thickness

There are also other known factors which contribute to errors in ultrasonic velocity measurements. One such error source relates to the variance of the thickness of the fluid-filled wheel surfaces about their circumference. More specifically, it is known that the time of flight of an ultrasonic signal varies as a function of the particular medium through which the signal propagates. Thus, the time of flight of an ultrasonic signal in a fluid will be different from the time of the flight of such an ultrasonic signal in other mediums, for example, the surfaces of the ultrasonic wheels about their circumference. Thus, a variance in the wheel thickness about its circumference will affect the transit times of ultrasonic signals in the acoustical path. As such, any mechanical property determinations based upon such ultrasonic measurements will include errors due to the variance in the wheel thickness. In order to compensate for this variance, the ultrasonic signals are averaged for a predetermined number of revolutions of the fluid-filled wheels; for example, one or two revolutions. By averaging the ultrasonic signals for a predetermined number of revolutions of the fluid-filled wheels, the effect of variance in the wheel thickness about its circumference is effectively minimized.

The Method

The method for improving the accuracy of time of flight measurements and minimizing the effects of the error sources mentioned above is best understood with reference to FIG. 4 which illustrates the acoustical path of the ultrasonic signals of interest for the conditions with and without a sample 26 present in the nip 28 between the fluid-filled wheels 22 and 24. The actual ultrasonic signals of interest, both transmitted and reflected, are illustrated in FIGS. 5A and 5B.

Figure 4:
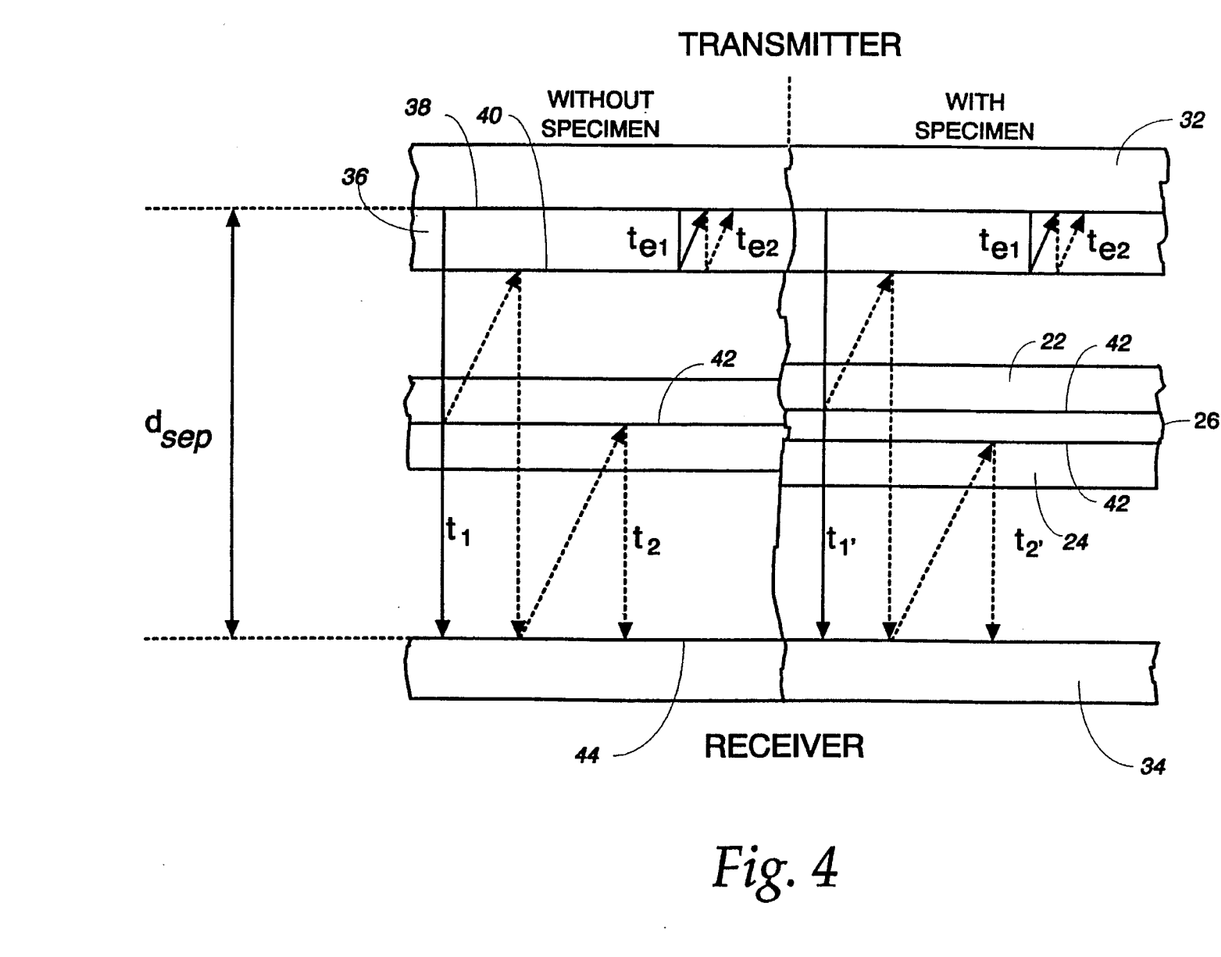
FIG. 4 is a simplified diagram of the ultrasonic system of FIG. 1, illustrating the acoustical path and flight times of various ultrasonic signals of interest.
Figure 5A:
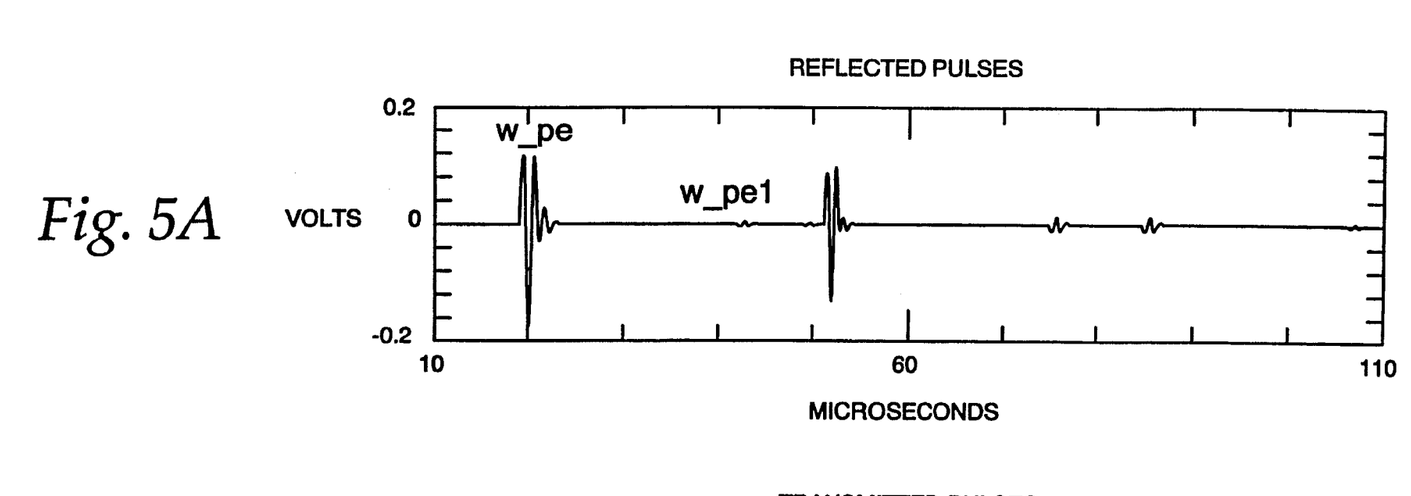
FIG. 5A is a graphical representation of the reflected-ultrasonic signals of interest.
Figure 5B:
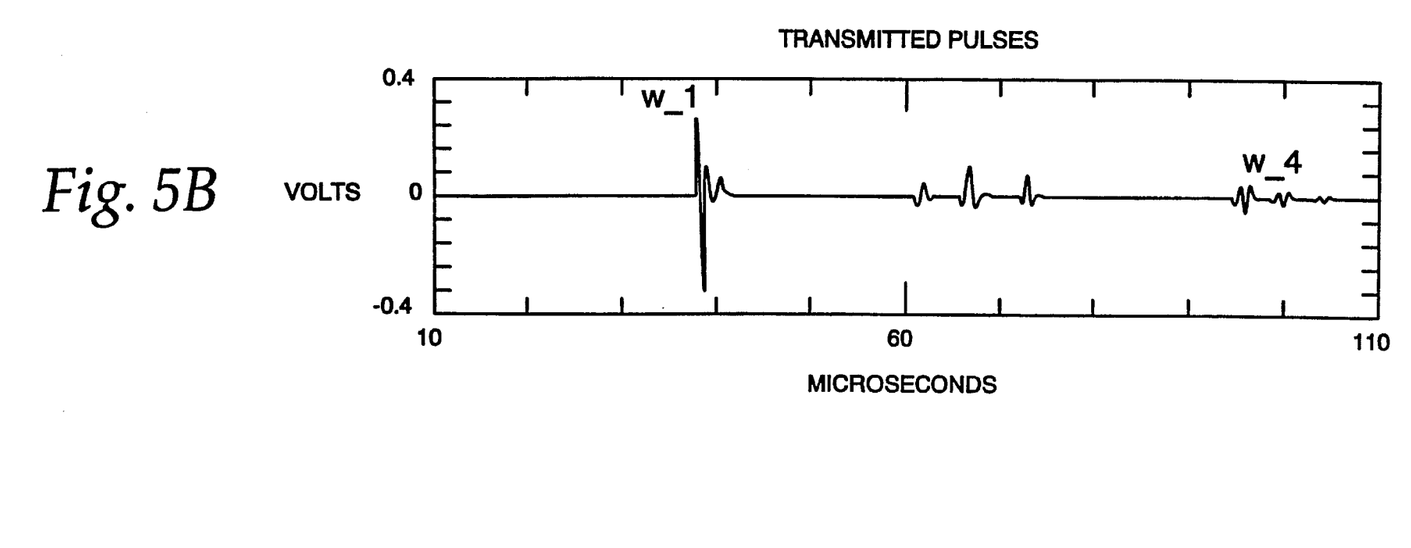
FIG. 5B is similar to FIG. 5A and illustrates the transmitted ultrasonic signals of interest.

As shown in FIG. 4, each of the fluid-filled wheels 22 and 24 contains an immersion-type ultrasonic transducer 32 and 34, respectively. In particular, the upper wheel 22 includes an ultrasonic transmitter/receiver 32, while the lower wheel 24 includes an ultrasonic receiver 34. The transmitter/receiver 32 enables various transmitted and reflected ultrasonic signals to be cross-correlated during a single sample period, thus eliminating any error in the time of flight measurement due to trigger jitter.

In order to compensate for changes in the fluid temperature in the fluid-filled wheels 22 and 24, an acrylic rod or shim 36 is disposed to be in contact with the surface of the transmitter 32. As is known in the art, the time of flight of the ultrasonic signal within the shim 36 is proportional to the shim temperature. For example, in a known system, it has been determined that a temperature increase of 1° C. in the fluid can change the signal propagation velocity by approximately 2.4 meters per second. Since the shim temperature represents the fluid temperature, the time of flight of the ultrasonic signal within the shim 36 may be used to compensate for changes in the fluid temperature of the fluid-filled wheels 22 and 24. By compensating for changes in the fluid temperature, the accuracy of the system can be significantly improved. A detailed description of the shim and its use in providing temperature compensation in such ultrasonic systems is described in "ON MACHINE SENSORS TO MEASURE PAPER MECHANICAL PROPERTIES" by Dr. Maclin S. Hall, Nov. 11, 1991, hereby incorporated by reference.

The ultrasonic signals of interest are defined in terms of the acoustical boundaries illustrated in FIG. 4. These acoustical boundaries are identified with the reference numerals 38 through 42. The first boundary 38 is the interface between the surface of the transmitter 32 and the shim 36. The second boundary 40 relates to the shim/water boundary. The reference numeral 42 is used to generally refer to the boundary between the fluid-filled wheels 22 and 24 and the web-like material 26. Lastly, the reference numeral 44 is utilized to represent the boundary at the surface of the receiver 34.

The first ultrasonic signal of interest is a transmitted signal w_1, identified in FIG. 4 as $t_1$. The signal w_1 is generated by the transmitter 32 and propagates through the shim 36 and is transmitted through the fluid in the upper fluid-filled wheel 22 across the interface 42 between the two fluid-filled wheels 22 and 24 and, in turn, is transmitted to the fluid in the lower fluid-filled wheel 24 and into the receiver 34. There are several other signals, partially reflected and partially absorbed at the various boundaries in the acoustic path that are also of interest. First, there is a signal that is partially reflected from the shim/water boundary 40 and, in turn, partially absorbed by the transmitter 32. This signal is identified as w_pe and illustrated in FIG. 4 as $te_1$. That portion of the reflected signal not absorbed by the transmitter 32 is reflected from the transmitter surface 38 to the shim/water boundary 40 and finally absorbed by the transmitter 32. This signal is identified as w_pel and illustrated in FIG. 4 as $te_2$. The last signal of interest is a partial reflection of the signal not transmitted through the nip 28 through the fluid-filled wheels 22 and 24, but reflects off the boundary 42 and, in turn, is reflected again from the shim/water boundary 40 to the surface 44 of the receiver 34 and again reflected from the surface 44 of the receiver 34 to the nip boundary 42 and finally absorbed by the receiver 32. This signal is identified as w_4 and illustrated in FIG. 4 at $t_2$.

The ultrasonic signals of interest described above are used to determine the various mechanical properties of the web 26 while eliminating errors due to trigger jitter. In addition, as will be described below, the signals are averaged for a predetermined number of revolutions of the fluid-filled wheels 22 and 24 in order to minimize any errors due to variance in the thickness of the wheels 22 and 24 about the circumference. Moreover, since the temperature of the fluid in the fluid-filled wheels 22 and 24 can affect the accuracy of the system, temperature compensation is provided. More particularly, the temperature of the fluid in the fluid-filled wheels 22 and 24 may be represented by the temperature of the shim 36. Since the temperature of the shim 36 is related to the time of flight of an ultrasonic signal through the shim 36, the shim flight time $t_{shim}$ is determined. The shim flight time $t_{shim}$ is determined by cross-correlating the ultrasonic signals w_pe and w_pe1 discussed above. Referring to FIG. 4, the shim flight time $t_{shim}$ may be represented by the arrival time of the signal w_pe1 relative to the arrival of time of the signal w_pe or $te_2-te_1$. Since these signals w_pe and w-pe1 are converted to digital values during the same sample period (e.g., not compared with stored values), the value of the shim flight time $t_{shim}$ will be free of any errors associated with trigger jitter.

In a similar manner, the errors due to trigger jitter are also eliminated from the time of flight or transit time measurements of ultrasonic signals between the transducers 32 and 34, both with and without a sample present. In particular, either the ultrasonic signal w_1, represented in FIG. 4 as $t_1$, corresponding to a condition without a sample present or the signal identified as $t_1'$ corresponding to a condition with a sample present is cross-correlated with an echo pulse w_pe, illustrated as $te_1$ in FIG. 4, first without a sample 26 present to obtain a reference value and then with a sample 26 present. The difference in these values, t_pe_1_del, is then used to determine the transit time through the sample 26.

The difference t_pe_1_del is free of errors due to trigger jitter. More particularly, the value $(t_1-te_1)$ without a sample present is determined by cross-correlating the signals w_1 and w_pe during the same sampling period. Thus, the quantity $(t_1-te_1)$ is free of any error due to trigger jitter. Similarly, the quantity $(t_1'-te_1)$ with a sample present is also determined by cross-correlating signals in the same sample period, thus eliminating any error due to trigger jitter in the quantity $(t'_1-te_1)$. Therefore, the difference between the quantities $(t_1'-te_1)-(t_1-te_1)$ will likewise be free of error due to trigger jitter.

The signals of interest can be manipulated to determine the time of flight through the web 26. In particular, the transit time through the sample 26 may be expressed mathematically as illustrated in Equation (1) as follows:

$$del\_ts = t\_pe\_1\_del + del\_d/f\_vel \quad (1)$$

where, del_ts=transit time through the sample, del_d=thickness or caliper of sample, f_vel=effective fluid velocity, t_pe_1_del=difference in sample time with and without a sample present as discussed above.

The caliper del_d may be determined by measurement or by cross-correlating the signals w_1 and w_4 without a sample present, represented as $t_1$ and $t_2$ in FIG. 4, and then cross-correlating the same signals with a sample present, represented as $t_1'$ and $t_2'$ in FIG. 4. Since the signals w_1 and w_4 during each of the conditions are cross-correlated during the same sample period, no errors will be present due to trigger jitter.

Expressed mathematically, the caliper del_d is given by Equation (2) below.

$$del\_d * [(t_2-t_1)-(t_2'-t_1')] f\_vel/2 \quad (2)$$

The manipulations (e.g., cross-correlations) described above may be carried out by the system illustrated in FIG. 1 by manipulation of the transit times of the ultrasonic signals of interest in the manner set forth below. In particular, the cross-correlations of the ultrasonic signals determine the relative flight times of various ultrasonic signals relative to various other ultrasonic signals discussed below. However, the system is first calibrated. Once the system is calibrated, the ultrasonic velocity through the sample 26 may be determined.

Calibration

The calibration is initiated by increasing the temperature in the fluid-filled wheels 22 and 24. The temperature of the fluid within the fluid-filled wheels 22 and 24 is increased by rotating the wheels 22 and 24 at a relatively high speed for a predetermined time period, for example, 30 minutes. Subsequently, the speed of the fluid-filled wheels 22 and 24 is slowed down, for example, to 2 revolutions per minute. During the cool-down period, various measurement pairs are taken in order to enable the fluid velocity to be determined as a function of the fluid temperature in the fluid-filled wheels 22 and 24.

Figure 6A:
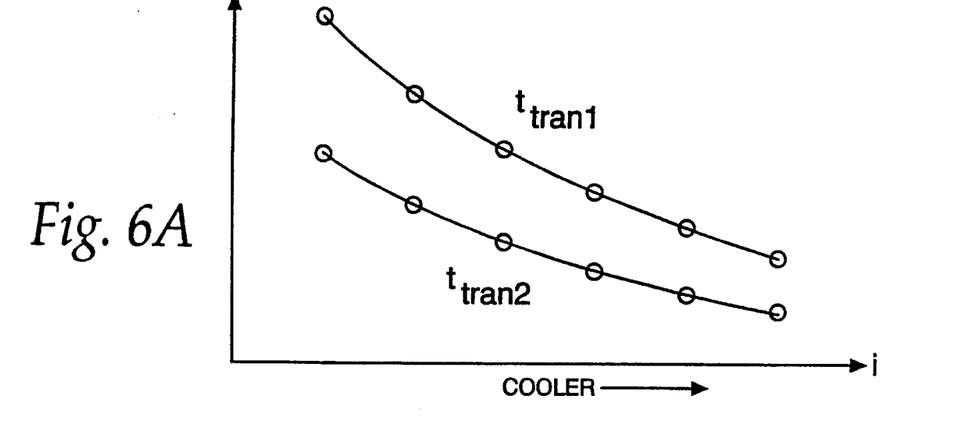
FIG. 6A is a graphical representation of the transit times $t_{tran1}$ and $t_{tran2}$ between transducers as a function of fluid temperature at two transducer separation distances.
Figure 6B:
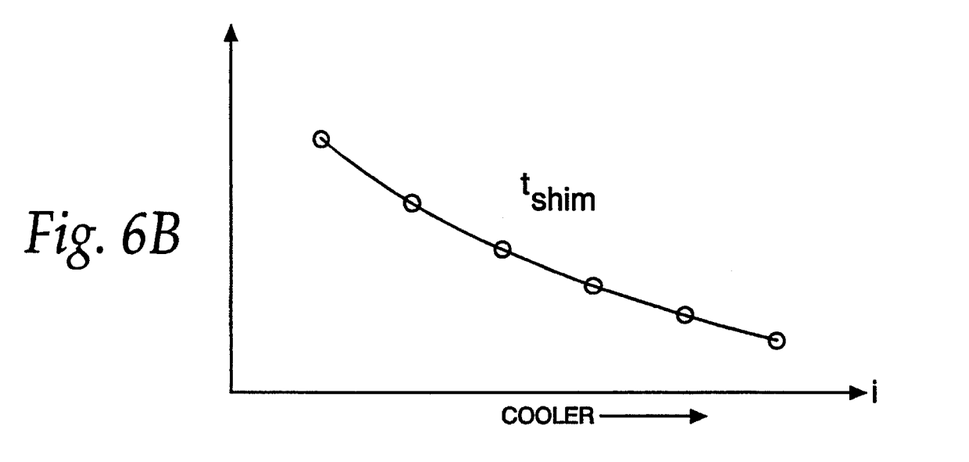
FIG. 6B is similar to FIG. 6A illustrating the relationship between the shim flight time $t_{shim}$ as a function of fluid temperature.
Figure 6C:
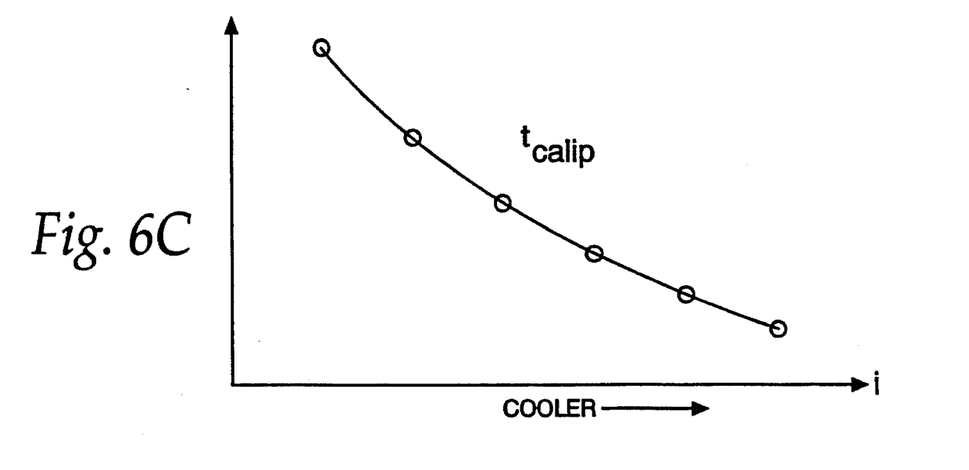
FIG. 6C is similar to FIG. 6A illustrating the transit time $t_{calip}$ as a function of fluid temperature.

In particular, it is known that the fluid velocity of an ultrasonic signal varies as a function of the fluid temperature which may vary for various reasons including friction and ambient conditions. As discussed above, the fluid temperature is directly related to the flight time $t_{shim}$ of an ultrasonic signal through the shim 36. In order to accurately determine the fluid velocity as a function of fluid temperature, the separation distance $d_{sap}$ between the transducers 32 and 34 is varied while the transit time $(t_{tran}=t_1-te_1)$ between transducers is recorded during the cool down. By providing a relatively precise measurement of the separation distance $d_{sap}$, the fluid velocity $V_{fluid}$ can be rather accurately determined. More particularly, with reference to FIG. 6A, the values of $t_{tran1}(i)$ and $d_{sap1}(i)$ are recorded during the cool down at a first predetermined separation distance between the transducers 32 and 34. Subsequently, the separation distance between the transducers 32 and 34 is decreased, for example, by about 2 millimeters, and the values of $t_{tran2}(i)$ and separation distance $d_{sap2}(i)$ are recorded as a function of the cool down. The shim flight time $t_{shim}(i)$ and caliper flight time $(t_{calip}=t_2-t_1)$ are also recorded during cool-down.

Figure 7A:
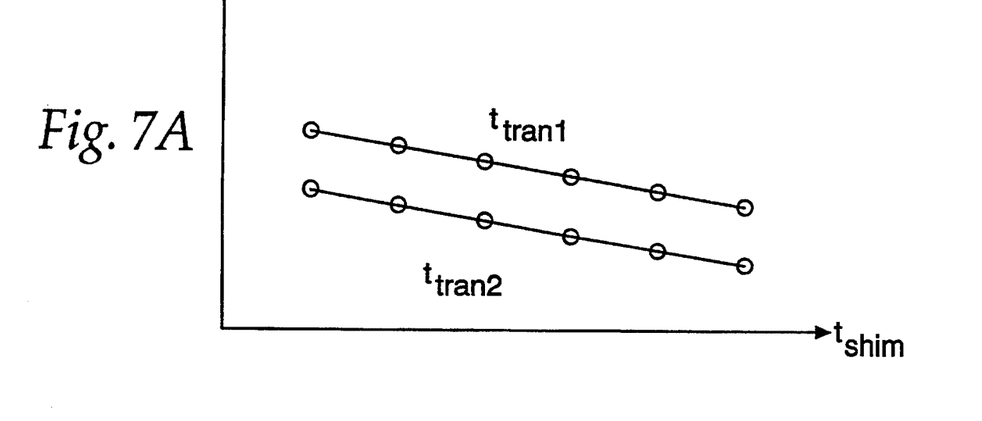
FIG. 7A is a graphical representation of the transit times $t_{tran1}$ and $t_{tran2}$ as a function of shim flight time $t_{shim}$.
Figure 7B:
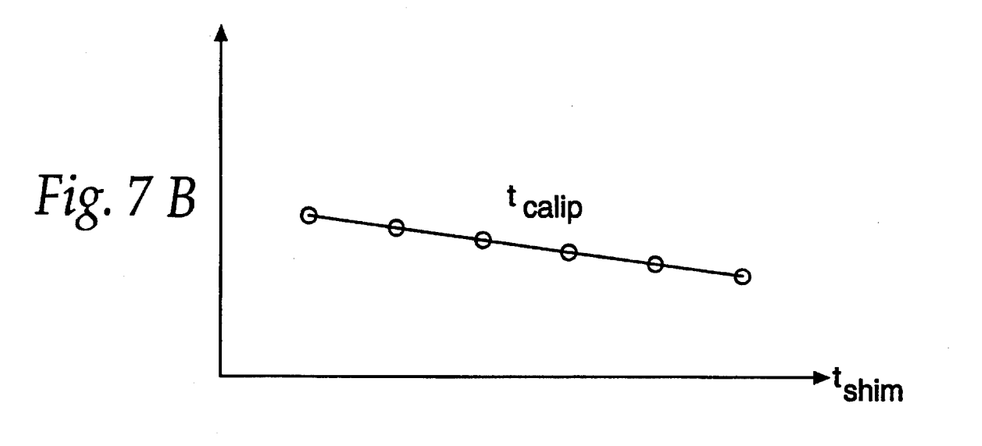
FIG. 7B is similar to FIG. 7A illustrating transit time $t_{calip}$ as a function of shim flight time $t_{shim}$.

In order to establish a relationship between the transmitted flight time $t_{tran}$ as a function of shim flight time $t_{shim}$, the curve $t_{tran1}$ and $t_{tran2}$ are combined with the curve $t_{shim}$ in order to form the composite curve illustrated in FIG. 7A which illustrates the relationship between the transmit time $t_{tran}$ and shim flight time $t_{shim}$. In a similar manner, the curve $t_{calip}$ is combined with the shim flight time $t_{shim}$ to form the composite illustrated in FIG. 7B.

Figure 8:
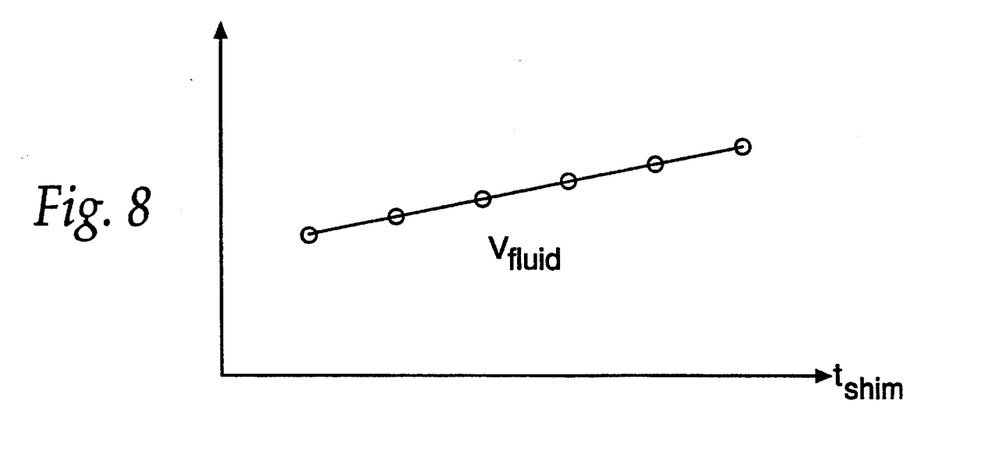
FIG. 8 is a graphical representation of fluid velocity $V_{fluid}$ as a function of shim flight time $t_{shim}$.

The fluid velocity as a function of shim flight time may then be determined in accordance with Equation (3) as follows and as illustrated in FIG. 8.

$$v_{fluid}(t_{shim}) = \frac{t_{tran1} - t_{tran2}}{d_{sep1} - d_{sep2}} \quad (3)$$

where, $V_{fluid}(t_{shim})$=the fluid velocity as a function of shim flight time, $t_{tran1}$= signal transit time between transducers at a first predetermined separation distance $d_{sep1}$ between transducers, $t_{tran2}$= signal transit time between transducers at a second predetermined separation distance $d_{sep2}$ between transducers, $d_{sep1}$= first predetermined separation distance between transducers, and $d_{sep2}$= second predetermined separation distance between transducers.

However, it is known that small changes in the separation distance $d_{sep}$ between the transducers 32 and 34 can occur (in addition to the selected separation distances $d_{sep1}$ and $d_{sep2}$ discussed above) as a result of cool down of the fluid temperature, sample testing and the relatively high RPM rates of the fluid-filled wheels 22 and 24. Since such changes in the separation distance can affect the accuracy of the system, a relationship between transmitted flight time $t_{tran}$ and shim flight time $t_{shim}$ is required. In particular, either $t_{tran1}$ or $t_{tran2}$ versus $t_{shim}$ may be used. In order to derive a relatively accurate relationship, each value of $t_{tran1}(i)$ must be normalized to some constant separation distance $d_{sep}'$, which may be arbitrarily selected as $d_{sep1}$. The normalization may be represented mathematically as illustrated in Equation (4).

$$t_{trans'}(t_{shim}) = t_{tran1} - \frac{d_{sep1} - d_{sep'}}{v_{fluid}} \quad (4)$$

where, $t_{tran'}$, $(t_{shim})$= normalized transit time as a function of shim flight time, $t_{tran1}$=signal transit time between transducers at a first predetermined separation distance between transducers, $d_{sep1}$=first predetermined separation distance between transducers, $V_{fluid}$= fluid velocity, and $d_{sep}$= constant separation distance.

In addition, a relationship must also be established between the transit times $t_{calip}$ and $t_{shim}$. The transit time $t_{calip}$ is a cross-correlation between the signals w_1 and w_4 (e.g., the arrival time of the signal w_1 relative to the arrival time of the signal w_4). Since the signal w_4 travels the distance between the shim 36 and the receiver 34 three times rather than one, any change in the separation distance between the transducers 32 and 34 will cause the signal w_4 to travel three times the change in separation distance through the extra fluid. Moreover, $t_{calip}$ depends upon the arrival time of signal w_1. The signal w_1 travels only the extra separation distance. Thus, the normalized transit time $t_{calip}$, as a function of shim flight time can be expressed mathematically, as illustrated in Equation (5).

$$t_{calip'}(t_{shim}) = t_{calip} - 2 * \frac{d_{sep1} - d_{sep'}}{v_{fluid}} \quad (5)$$

where, $t_{calip'}(t_{shim})$= normalized transit time as a function of shim flight time, $t_{calip}$= arrival time of signal w_1 relative to the arrival time of signal w_4, $d_{sep1}$=transducer separation distance at a first predetermined value, $d_{sep}$= constant separation distance, and $V_{fluid}$=fluid velocity.

Operation

Once the system is calibrated as discussed above, a sample 26 is disposed in the nip 28 defined between the fluid-filled wheels 22 and 24 and the system is ready to perform on-line testing of the moving web 26. In particular, the determination of the velocity and time of flight of an ultrasonic signal through the sample may be determined while the web 26 is moving by cross-correlating various ultrasonic signals as discussed above. This method of determining the time of flight and velocity of an ultrasonic signal through the web 26 is practically implemented by measuring the flight times of various ultrasonic signals and manipulating the flight time measurements in the manner set forth below.

In particular, an initial assumption is made that the difference between normalized transit time $t_{tran'}$ ($t_{shim}$) obtained during calibration without the presence of a sample 26 and transit time $t_{tran}$ with a sample present is representative of the transit time of an ultrasonic signal through the sample 26. However, this assumption ignores the following three factors: 1) the transducer separation distance is not constant; 2) the temperature of the fluid in the wheels is not constant; and 3) the presence of the sample shortens the pulse propagation path in the fluid by an amount equal to the caliper of the sample.

In order to provide a relatively accurate determination of the flight time of an ultrasonic signal through a sample, the transmit time is compensated for the three factors mentioned above. In particular, in order to compensate for the variance in the separation distance of the transducers 32 and 34, the change in the fluid path time through the extra fluid distance created by the increase/decrease of the separation distance is determined. This change is shown mathematically in Equation (6).

$$tx_1 = \frac{d_{sep} - d_{sep'}}{V_{fluid}(t_{shim})} \quad (6)$$

where, $tx_1$= change in fluid path time, $d_{sep'}$= the constant separation distance of transducers, $d_{sep}$=the presently measured separation distance, $V_{fluid(tshim)}$=the relation derived from the calibration which accounts for temperature variations, and $t_{shim}$=presently measured shim flight time.

In order to determine the velocity and time of flight of an ultrasonic signal through the sample, the flight time of the signal w_4 with no sample 26 present is determined by first breaking down the travel time into its respective component travel times through each media. More particularly, as illustrated in Equation (7).

$$t_2 = t'_{shim} + t_{fluid(top)} + t_{wheel(top)} + t_{wheel(top)} + t_{fluid(top)} + \quad (7)$$
$$t_{fluid(top)} + t_{wheel(top)} + t_{wheel(bottom)} + t_{fluid(bottom)} +$$
$$t_{fluid(bottom)} + t_{wheel(bottom)} + t_{wheel(bottom)} + t_{fluid(bottom)}$$

where, $t_2$= transit time of signal w_4, $t'_{shim}$=transit time through shim 36, where $t_{shim}=2t'_{shim}$, $t_{fluid(top)}$=transit time through fluid in upper wheel 22, $t_{wheel(top)}$=transit time through thickness of upper wheel 22, $t_{wheel(bottom)}$= transit time through thickness of lower wheel 24, and $t_{fluid(bottom)}$=transit time through fluid in lower wheel 24.

Similarly, the transit time of the signal w_1 may also be broken down into its component parts as set forth in Equation (8).

$$t_1 = t'_{shim} + t_{fluid(top)} + t_{wheel(top)} + t_{wheel(bottom)} + t_{fluid(bottom)} \quad (8)$$

The difference between Equations (7) and (8) is $t_{calip}$, as set forth in Equation (9).

$$t_{calip} = 2*(t_{fluid(top)} + t_{wheel(top)} + t_{wheel(bottom)} + t_{fluid(bottom)}) \quad (9)$$

When a sample is placed in the nip 28 between the wheels 22 and 24, the equivalent difference ($t_{calip'}$) is the same, with the exception that the sample 26 displaces some of the distance otherwise traveled in the fluid. Thus, the difference $t_{calip'} - t_{calip}$ is the amount of time that the ultrasonic signal does not travel in the fluid due to the presence of the sample 26. Accordingly, the fluid travel distance displaced by sample ($d_{samp}$) is provided in Equation (10).

$$2*d_{samp} = V_{fluid}*(t_{calip'} - t_{calip}) \quad (10)$$

In addition, it is necessary to account for any changes in the shim flight time $t_{shim}$ and the separation distance between the transducers 32 and 34. Thus, the equation for caliper of the sample 26 is given by Equation (11).

$$d_{samp} = \frac{V_{fluid}(t_{shim})}{2} * (t_{calip'}(t_{shim}) - t_{calip}) - (d_{sep} - d_{sep1(1)}) \quad (11)$$

Moreover, in order to account for the third factor mentioned above, it is necessary to subtract the fluid path flight time through the fluid path occupied by the sample. This fluid path time is given by Equation (12).

$$tx_2 = \frac{d_{samp}}{V_{fluid}(t_{shim})} \quad (12)$$

where, $d_{samp}$ = presently measured caliper thickness. The flight time through the sample requires that Equation (6) be added and Equation (12) be subtracted from the difference between $t_{tran}$ and $t_{tran}'$ ($t_{shim}$). The resulting Equation (13) thus provides the calculation of the flight time of an ultrasonic signal through the sample which accounts for the three factors mentioned above.

$$t_{samp} = t_{tran} - t_{tran'}(t_{shim}) + \frac{d_{sep} - d_{sep1(1)}}{V_{fluid}(t_{shim})} - \frac{d_{samp}}{V_{fluid}(t_{shim})} \quad (13)$$

The ultrasonic velocity through the sample is simply given in Equation (14).

$$v_{samp} = \frac{d_{samp}}{t_{samp}} \quad (14)$$

The method described above provides a relatively precise indication of the ultrasonic velocity and time of flight of an ultrasonic signal through a sample 26 while avoiding any errors resulting from trigger jitter of the digitizing oscilloscope. In addition, as will be discussed in more detail below, errors due to variances in the thickness of the fluid-filled wheels 22 and 24 are also minimized by averaging signals over a predetermined period, for example one or more revolutions of the fluid-filled wheels.

By providing a relatively precise method for determining the velocity and flight times of an ultrasonic signal through a sample, testing of various mechanical properties of a moving web becomes more viable to the industry. By providing a method that enables on-line and relatively accurate testing of a moving web, the overall time and cost of producing webs of paper, paperboard and the like is greatly reduced.

The System

An exemplary system 20 for implementing the method described above is illustrated in FIG. 1. The system includes the pair of immersion-type ultrasonic transducers 32 and 34, disposed within fluid-filled wheels 22 and 24, respectively, as discussed above. The ultrasonic transducers 32 and 34 may be formed from either ceramic or plastic piezoelectric materials. Such immersion transducers may be purchased from either Panametrics Corporation of Waltham, Mass. or Dapco Industries of Ridgefield, Conn. The fluid-filled wheels 22 and 24 are typically 7 inches in diameter and ⅜ inch thick; for example, as manufactured by Dapco Industries. The transducers 32 and 34 are rigidly affixed to the axis (not shown) about which the wheels 22 and 24 rotate. The wheels 22 and 24 are disposed such that their respective axes of rotation are parallel and spaced apart such that the wheels 22 and 24 are in contact when no sample 26 is present.

Since relatively small variances in the separation distance between the transducers 32 and 34 can cause errors in the time of flight measurements, as discussed above, an inductive distance measurement system 46 is incorporated to continuously monitor the distance between the transducers 32 and 34 in order to provide repetitive correction for variations in the transducer separation distance, thereby increasing the accuracy of the calculated velocities. The inductive measurement system 46, for example, a Kaman Instrumentation Corporation Model No. KD-2300-6C, includes a conductive metal target 48 attached to a support 50 which, in turn, is connected to the upper wheel 22. An inductive-type sensor 52 is attached to a support 54 connected to the lower wheel 24. The inductive measurement system 46 provides a voltage output proportional to the separation distance between the conductive target 48 and the inductive sensor 52 and, hence, the transducers 32 and 34. A detailed description of such an inductive measurement system 46 is provided in detail *Part I The Work Book Applications Information,* pp. 5–13 by the Kaman Instrumentation Corporation, hereby incorporated by reference.

As shown in FIG. 1, the output voltage of the inductive measurement system 46 is applied to a digital voltmeter 56, for example, a Hewlett Packard Model No. 3478A programmable digital voltmeter by way of an electric cable 58. The voltmeter 56 includes an internal analog-to-digital converter (not shown) for digitizing the output voltage from the inductive measurement system 46. The voltmeter 56 also includes an internal interface bus and an external connector which meet IEEE Standard 488-1978 to enable the output of the digital voltmeter 56 to be applied to an input/output port of a digital computer 60, by way of a general purpose interface bus (GPIB) 62.

A detailed description of a digital voltmeter suitable for the above-mentioned application is described in detail in *Meet the 3478A,* pp. 1–83, by the Hewlett Packard Company. A suitable GPIB may be purchased from National Instruments Company, for example, a Model No. GPIB-PCIIA. The digital computer 60 is preferably an IBM or IBM-compatible personal computer based on an Intel 80386 microprocessor, or better.

In addition to providing an interface between the digital voltmeter 56 and the digital computer 60, the GPIB 62 also provides an interface between a digitizing oscilloscope 64 and the digital computer 60. The digitizing oscilloscope 64, for example, a LeCroy Series 7200 precision digital oscilloscope is utilized to monitor the ultrasonic signals of interest discussed above. In addition, the digitizing oscilloscope 64 includes an analog-to-digital converter (not shown) for converting the signals of interest to digital values for transmission to the digital computer 60 by way of the GPIB 62. In particular, the digitizing oscilloscope 64 is provided with two channels. As shown in FIG. 1, the system is configured such that transmitted signals are applied to channel I and reflected signals are applied to channel 2.

The analog-to-digital conversion process in the digitizing oscilloscope 64 is under the control of an external trigger which, in turn, is under the control of a pulse echo box 66. The pulse echo box 66, for example, a Model No. 5055PR manufactured by Panametrics, is adapted to generate predetermined single cycle electric pulses which, when applied to an ultrasonic transducer, such as the ultrasonic transducer 32, are converted into ultrasonic signals. The pulse echo box 66 includes a dual-purpose I/O line 68 which outputs a relatively short duration ultrasonic pulse in response to an external trigger and is also able to accept ultrasonic echo pulses to enable the transmitter 32 to act as a receiver as well. The echoes are available at the signal output line of the pulse echo box 66 which, in turn, is applied to channel 2 of the digitizing oscilloscope 64.

The transmitted pulses are applied to channel 1 of the digitizing oscilloscope 64 by way of an ultrasonic preamp 70. The ultrasonic preamp 70 may be, for example, a Model No. 5662 manufactured by Panametrics in Waltham, Mass. The external trigger of the digitizing oscilloscope 64 is under the control of the dual-purpose I/O line 68. By connecting the external trigger of the digitizing oscilloscope 64 to the dual-purpose I/O line 68, the oscilloscope 64 will be triggered any time an ultrasonic pulse is transmitted from or received at the transducer 32.

The pulse echo box 66 is triggered by a four-state state machine generally identified with the reference numeral 72. The state machine 72 in conjunction with a proximity sensor system 74, used to sense the revolutions of the fluid-filled wheel 22, are used to generate a trigger signal for the pulse echo box 66. In particular, the state machine 72 enables the ultrasonic signals of interest as discussed above to be averaged for a predetermined number of revolutions of the fluid-filled wheels 22 and 24. As described below, the ultrasonic signals of interest are averaged for a single revolution, for example, of the fluid-filled wheel 22 during every fourth revolution. However, the principles of the invention are clearly applicable to other averaging configurations. Averaging of the ultrasonic signals for a predetermined number of revolutions of the fluid-filled wheel 22 minimizes errors in time of flight measurements which result from variances in the thickness of the wheels 22 and 24 about their circumference.

Figure 9A:
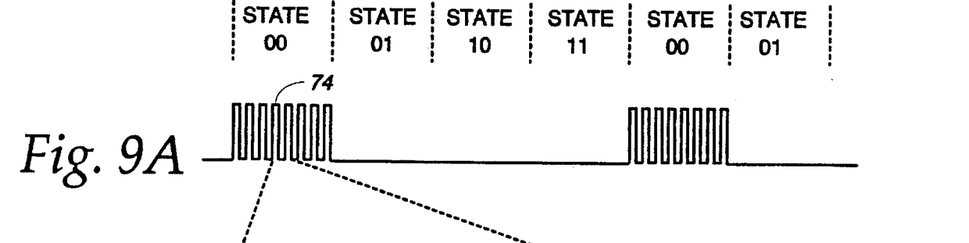
FIG. 9A represents the trigger signals applied to the pulse/echo box during one sample period in accordance with the method in accordance with the present invention.
Figure 9B:
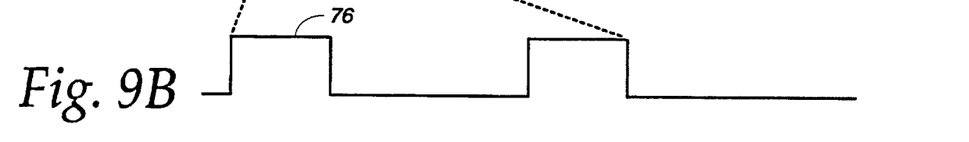
FIG. 9B represents an exaggerated data sample period in response to one trigger signal as illustrated in FIG. 9A.
Figure 9C:
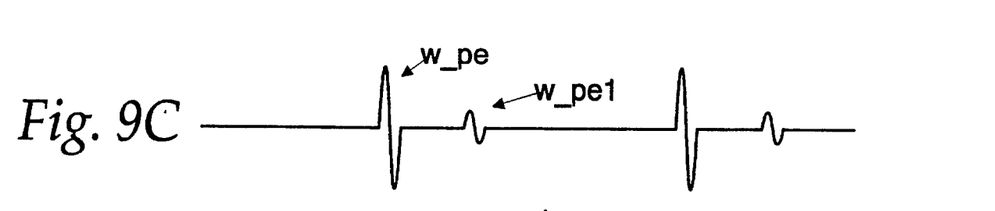
FIGS. 9C and 9D are timing diagrams illustrating various ultrasonic signals of interest.
Figure 9D:
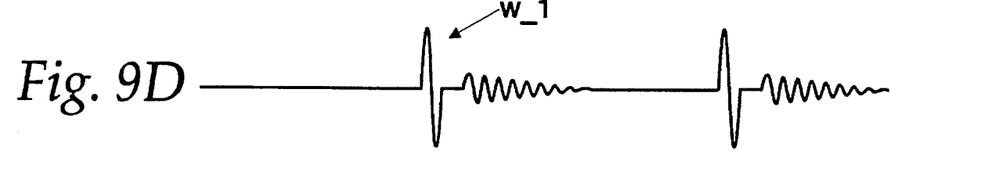

The averaging of the ultrasonic signals of interest under the control of the state machine 72 is best understood with reference to FIGS. 9A through 9G. Referring to FIG. 9A, each revolution of the fluid-filled wheel 22 as sensed by the proximity sensor system 74 is used to define a state. As shown, four binary states are shown with signal acquisitions being made during one revolution out of every four revolutions (e.g., during state 00). This is accomplished by utilizing the state machine 72 as a trigger for the pulse echo box 66. Thus, as shown in FIG. 9A, a plurality of trigger pulses 74 are illustrated during state 00. Each trigger pulse 74 results in a data acquisition or sample period 76 in which the digitizing oscilloscope 64 senses and digitizes the ultrasonic signals of interest as shown in FIGS. 9C and 9D. For clarity, only a single sample period 76 and corresponding signals during that sample period 76 are shown in FIGS. 9B through 9D. At the end of a sample period 76, there are three dead states: states 01; 10 and 11 available for wave transfer, cross-correlation, manipulation, including averaging and preparation for the next acquisition.

Figure 9E:
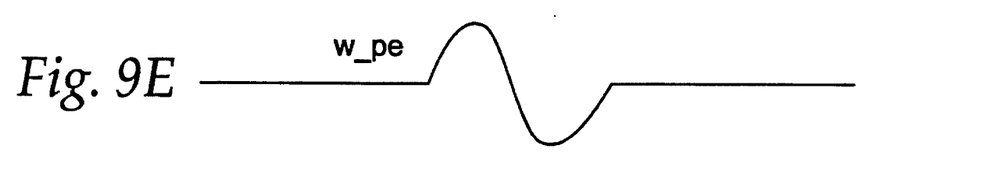
FIGS. 9E–9G are timing diagrams representing the averaged signal values during a single sample period in accordance with the method of the present invention.
Figure 9F:
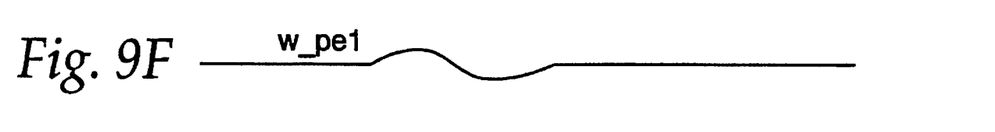
Figure 9G:
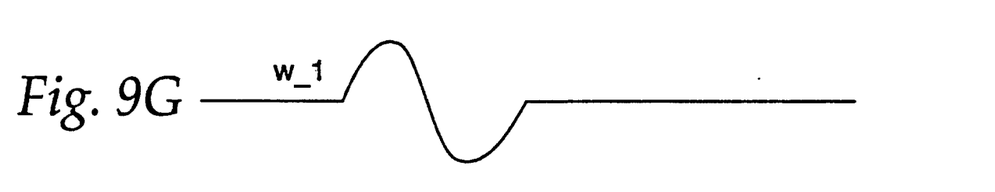

In order to minimize errors in the time of flight measurements due to the variance in the thickness of the fluid-filled wheels 22 and 24 about their circumference, the ultrasonic signals of interest illustrated in FIGS. 9C and 9D, acquired during every fourth revolution of the fluid-filled wheel 22 (e.g., state 00), are averaged for that period. The averaged signals illustrated in FIGS. 9E through 9G are thus used in the computations to minimize errors associated with the variance in thickness.

The state machine 72 includes a squarewave generator, for example, a 5-volt, 1 kHz generator 78, for example, a Dynascan Corporation Model 3020 sweep/function generator which produces a continuous train of single cycle pulses 74 that are applied to the input of a three-channel analog multiplexer 80. One of the multiplexer 80 outputs (output A2 as shown) is directly coupled to the trigger input of the pulse echo box 66 during every fourth revolution of the fluid-filled wheel 22 under the control of a four-state roll-around counter 82. The four-state roll-around counter 82 is under the control of the proximity sensor system 74 which includes a target 83, rigidly attached to the fluid-filled wheel 22 to rotate therewith, and a proximity sensor 86 disposed adjacent the fluid-filled wheel 22. Such proximity sensor systems 74 are generally known in the art. As configured in FIG. 1, the proximity sensor system 74 will generate a signal each time the target 83 is in proximity to the proximity sensor 86. This signal, in turn, is applied to the clock input of the four-state roll-around counter 82 to provide a clock signal every revolution of the fluid-filled wheel 22. The four-state roll-around counter 82 as discussed above counts the number of revolutions of the fluid-filled wheel 22 in order to control the analog multiplexer 80.

The state machine 72 also provides an input to the digital computer 60 by way of a bus 84 to enable the digital computer 60 to monitor the state of the state machine 72 in order to synchronize acquisition and communication with the GPIB interface 62 with rotation of the fluid-filled wheel 22. The count state of the state machine 72 is applied to an I/O port 86 in the digital computer 60. The count state is provided by the analog multiplexer 80 which applies a 5-volt input 87 to one of its outputs B1, B2 or B3 under the control of the four-state roll-around counter 82. The 5-volt input 87 is thus applied to the multiplexer outputs B1, B2 and B3 to signify the state of the state machine 72.

Figure 10:
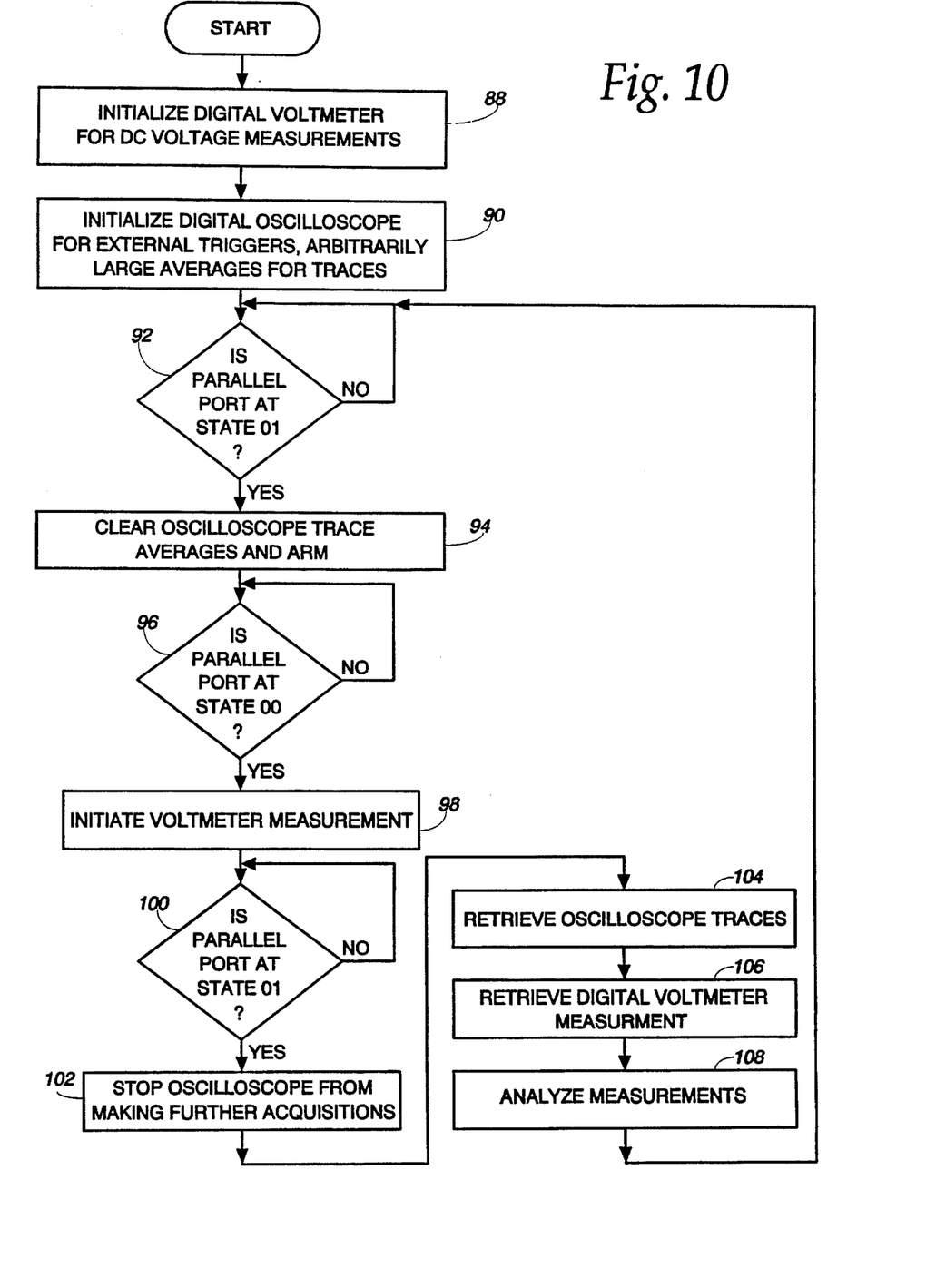
FIG. 10 is a flow diagram for use with the method according to the present invention.

The testing system 20, illustrated in FIG. 1, is under the control of the digital computer 60. A flow control diagram for the digital computer 60 is illustrated in FIG. 10. In particular, once the system 20 is started, the digital voltmeter 56 is initialized in step 88. Once the digital voltmeter 56 is initialized, the digitizing oscilloscope 64 is initialized for external triggers and arbitrarily large averages for signals in step 90. Next, the system determines the state of the state machine 72 and in particular whether the state machine 72 is at state 01 in step 92. Referring back to FIG. 9A, state 01 refers to the state in which data acquisitions by the digitizing oscilloscope 64 are disabled. This is done in order to initialize the digitizing oscilloscope 64. If the state machine 72 is not at state 01, the system cycles until state 01 is reached indicating that the acquisition period (e.g., state 00) is over. Once the system determines that the state machine is at state 01, the digitizing oscilloscope 64 is cleared in step 94 and armed for future acquisitions. The system then waits for the next data acquisition period by monitoring the I/O port 86 to ascertain when the system reaches state 00 in step 96. Once the system determines that the state machine is at state 00 in step 96, the system initiates voltmeter measurements by the digital voltmeter 56 by way of the GPIB interface 62. Data acquisitions are made during the sampling period (e.g., until state 01 is reached) as determined by the system in step 100. This is done by continuously monitoring the parallel I/O port 86 to determine when the state machine reaches 01. Once the state machine reaches state 01, data acquisitions are disabled for the next three states which correspond to the next three revolutions of the fluid-filled wheel 22. Accordingly, the digitizing oscilloscope 64 is disabled from making additional acquisitions in step 102. Subsequently, in steps 104 and 106, the acquired data from the digital voltmeter 56 and digitizing oscilloscope 64 are retrieved in steps 104 and 106, respectively. After the data from the digital voltmeter 56 and digitizing oscilloscope 64 is retrieved, this data is averaged in a known manner and manipulated by the digital computer 60 as discussed above in step 108. This manipulation continues during state 01 after which the cycle repeats.

The caliper or thickness ($d_{samp}$) of the web for use in the manipulations discussed above can be obtained in various ways, all of which are intended to be within the scope of the present invention. For example, a Measurex Model 2001 commercial caliper gauge, may be used to measure the caliper and interfaced to the digital computer 60 by way of a type CTM05 countertimer board.

Obviously, many modifications and variations of the present invention are possible in light of the above teachings. Thus, it is to be understood that, within the scope of the appended claims, the invention may be practiced otherwise than as specifically described above.

What is claimed and desired to be secured by letters patent of the United States is:

1. A system for making ultrasonic measurements on a moving web defining opposing planar surfaces of a predetermined material having a predetermined thickness, the ultrasonic measurements being made in a direction generally perpendicular to said opposing planar surfaces of the moving web, the system comprising:

a first ultrasonic transducer rigidly disposed about a first axis generally parallel to said moving web for transmitting predetermined ultrasonic signals in a direction generally perpendicular to said opposing planar surfaces and for receiving predetermined reflected ultrasonic signals whose transmit times are to be measured to determine ultrasonic velocities of said predetermined reflected ultrasonic signals;

a second ultrasonic transducer rigidly disposed about a second axis generally parallel to said moving web for receiving said predetermined ultrasonic signals transmitted by said first ultrasonic transducer, said first and second axes spaced apart so that each of said transducers is disposed adjacent a different opposing surface of said web;

means for coupling ultrasonic signals between said ultrasonic transducers and said moving web;

means for measuring the transmit times of said predetermined ultrasonic signals received by said second ultrasonic transducer and said predetermined reflected ultrasonic signals received by said first ultrasonic transducer, said measuring means including means for digitizing said predetermined ultrasonic signals received by said second ultrasonic transducer and said predetermined reflected ultrasonic signals received by said first ultrasonic transducer in response to one or more predetermined trigger signals;

means for triggering said digitizing means, said triggering means including means for generating said one or more predetermined trigger signals; and means for eliminating errors due to delays in the onset of digitization after the digitizing means has been triggered.

2. A system as recited in claim 1, wherein said coupling means includes a pair of fluid-filled wheels, said fluid-filled wheels filled with a predetermined fluid.

3. A system as recited in claim 2, further including means for compensating for temperature variations of said predetermined fluid in said fluid-filled wheels.

4. A system as recited in claim 1, wherein said eliminating means includes means for cross-correlating predetermined ultrasonic signals transmitted by said first ultrasonic transducer and received by said second ultrasonic transducer and said predetermined reflected ultrasonic signals received by said first ultrasonic transducer.

5. A system as recited in claim 4, wherein said cross-correlating means includes means for cross-correlating ultrasonic signals during predetermined time periods.

6. A system as recited in claim 5, wherein one or more of said predetermined time periods correspond to ultrasonic signals resulting from a single one of said one or more predetermined trigger signals.

7. A system as recited in claim 1, wherein said digitizing means includes a digitizing oscilloscope.

8. A system for making ultrasonic measurements on a moving web having opposing planar surfaces of a predetermined material comprising:

a first ultrasonic transducer rigidly disposed about a first axis generally parallel to said moving web for transmitting predetermined ultrasonic signals in a direction generally perpendicular to said opposing planar surfaces and receiving predetermined reflected ultrasonic signals;

a second ultrasonic transducer rigidly disposed about a second axis generally parallel to said moving web for receiving said predetermined ultrasonic signals transmitted by said first ultrasonic transducer, said first and second axes spaced apart so that each of said transducers is disposed adjacent a different opposing surface of said moving web;

means for coupling ultrasonic signals between said ultrasonic transducers and said moving web;

means for measuring the transmit times of said predetermined ultrasonic signals received by said second ultrasonic transducer and said predetermined reflected ultrasonic signals received by said first ultrasonic transducer to determine the ultrasonic velocities of said predetermined ultrasonic signals and said predetermined reflected ultrasonic signals, said measuring means including means for digitizing said predetermined ultrasonic signals received by said second ultrasonic transducer and said predetermined reflected ultrasonic signals received by said first ultrasonic transducer in response to a predetermined trigger signal;

means for triggering said digitizing means, said triggering means including means for generating said predetermined trigger signal; and means for eliminating errors relating to delays in the onset of digitization after said digitizing means has been triggered, wherein said eliminating means includes means for cross-correlating said predetermined ultrasonic signals received by said second ultrasonic transducer due to a single excitation pulse transmitted from said first ultrasonic transducer to said second ultrasonic transducer, with predetermined reflected ultrasonic signals received at said first ultrasonic transducer during one or more sample periods.

\* \* \* \* \*